(12) United States Patent
Choi

(10) Patent No.: US 12,324,586 B2
(45) Date of Patent: *Jun. 10, 2025

(54) APPARATUS AND METHODS FOR MANAGING A SHAPE OF A JUNCTION BETWEEN A BLADDER AND URETHRA

(71) Applicant: Levee Medical, Inc., Durham, NC (US)

(72) Inventor: Bruce Choi, Raleigh, NC (US)

(73) Assignee: LEVEE MEDICAL, INC., Durham, NC (US)

( * ) Notice: Subject to any disclaimer, the term of this patent is extended or adjusted under 35 U.S.C. 154(b) by 875 days.

This patent is subject to a terminal disclaimer.

(21) Appl. No.: 17/521,354

(22) Filed: Nov. 8, 2021

(65) Prior Publication Data

US 2022/0071636 A1 Mar. 10, 2022

Related U.S. Application Data

(63) Continuation-in-part of application No. 17/012,555, filed on Sep. 4, 2020, now Pat. No. 12,150,849.

(51) Int. Cl.
*A61F 2/00* (2006.01)
*A61B 17/11* (2006.01)

(52) U.S. Cl.
CPC ............ *A61B 17/11* (2013.01); *A61F 2/0022* (2013.01); *A61F 2/0036* (2013.01); *A61B 2017/1132* (2013.01)

(58) Field of Classification Search
CPC ............ A61B 17/11; A61B 2017/1132; A61F 2/0036; A61F 2/04; A61F 2/042; A61F 2002/047; A61F 2210/0014; A61F 2220/0008; A61F 2230/0067
See application file for complete search history.

(56) References Cited

U.S. PATENT DOCUMENTS

| 12,150,849 | B2 * | 11/2024 | Choi ............... A61B 17/11 |
| 2003/0229364 | A1 | 12/2003 | Seiba |
| 2015/0351767 | A1 | 12/2015 | Zoll et al. |
| 2016/0004283 | A1 | 1/2016 | Ganguly |
| 2017/0274123 | A1 * | 9/2017 | Rosell Gratacos ..... C23C 16/06 |

FOREIGN PATENT DOCUMENTS

WO    2016004283 A1    1/2016

OTHER PUBLICATIONS

David D. Childs, et al.; "Multimodality Imaging of the Male Urethra: Trauma, Infection, Neoplasm, and Common Surgical Repairs-Special section: Urothelial Disease", published on-line (Aug. 22, 2019) pp. 3935-3949;vol. 44, No. 12: https://doi.org/10.1007/s00261-019-02127-8; Abdominal Radiology, Springer US, New York.

S. F. Mungovan et al., Preoperative Membranous Urethral Length Measurement and Continence Recovery Following Radical Prostatectomy: A Systematic Review and Meta-analysis (HHS Public Access, Author mainuscript, EUR Urol. Mar. 2017; 71(3): pp. 368-378. doi: 10.1016/j.eururo.2016.06.023 (nih.gov)).

(Continued)

*Primary Examiner* — Christine H Matthews
(74) *Attorney, Agent, or Firm* — Duane Morris LLP

(57) ABSTRACT

The disclosure relates to apparatus and methods for managing a shape of a junction between a bladder and urethra, for example, to promote urinary continence after a prostatectomy.

20 Claims, 10 Drawing Sheets

(56) References Cited

OTHER PUBLICATIONS

V. W. Nitti, MD Rev Urol. 2001; 3(Suppl 1): S2-S6. The Prevalence of Urinary Incontinence (nih.gov).

Irwin et. al. BJU Int. Oct. 2011; 108(7): 1132-8 Global Forum on Incontinence, Sweden (2018) Worldwide prevalence estimates of lower urinary tract symptoms, overactive bladder, urinary incontinence and bladder outlet obstruction—Irwin—2011—BJU International—Wiley Online Library.

N. J. Sathianathen et al., An objective measurement of urinary continence recovery with pelvic floor physiotherapy following robotic assisted radical prostatectomy; Translational Andrology and Urology, vol. 6, Suppl Jul. 2, 2017—(amegroups.com).

K. Hoyland, et al., Post-Radical Prostatectomy Incontinence: Etiology and Prevention, Reviews in Urology. vol. 16 (4); 2014 https://www.ncbi.nlm.nih.gov/pmc/articles/PMC4274175/pdf/RIU016004_0181.pdf.

W.T. Lowrance et al., Contemporary open and robotic radical prostatectomy practice patterns among urologists in the United States (2012). The Journal of urology, 187(6), 2087-2092.—Abstract—Europe PMC.

B.T. Helfand, et al., Prevalence and Characteristics of Urinary Incontinence in a Treatment-Seeking Male Prospective Cohort—Results from the LURN Study; J Urol. Aug. 2018 ; 200(2): 397-404. (nih.gov).

B.S. Buckley et al., Prevalence of Urinary Incontinence in Men, Women, and Children-Current Evidence: Findings of the Fourth International Consultation on Incontinence; Urology vol. 76, Issue 2, Aug. 2010, pp. 265-270 https://www.sciencedirect.com/science/article/pil/80090429510000191.

S.P. Daugirdas, et al., Urinary Incontnence and Chronic Conditions in the US Population age 50 years and older; Int Urogynecol J. Jan. 3, 2020. doi: 10.1007/s00192-019-04137-y.

Gorina Y, Schappert S, Bercovitz A, et al. Prevalence of incontinence among older Americans. National Center for Health Statistics. Vital Health Stat 3(36). 2014. https://www.cdc.gov/nchs/data/series/sr_03/sr03_036.pdf.

\* cited by examiner

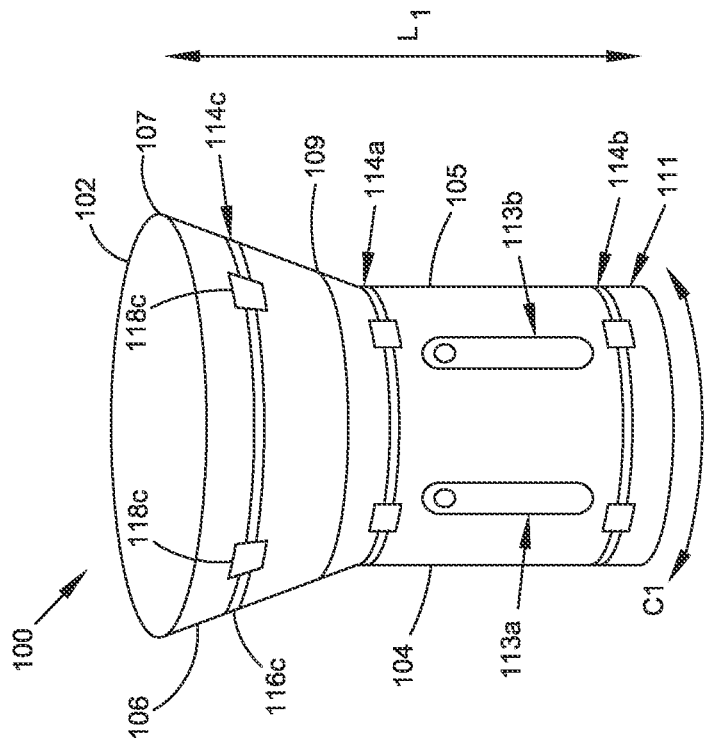
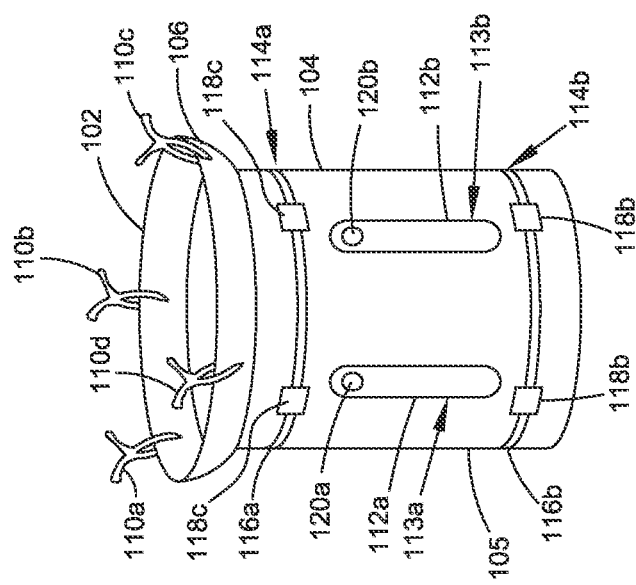

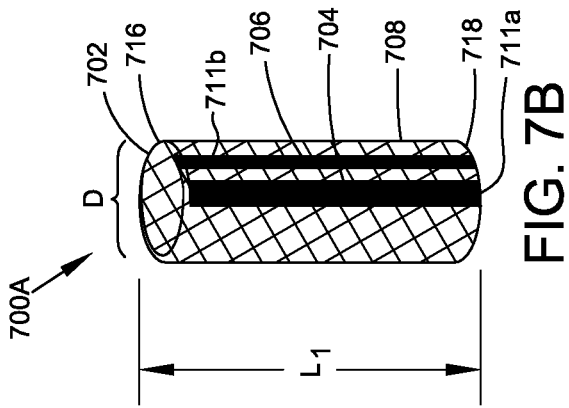
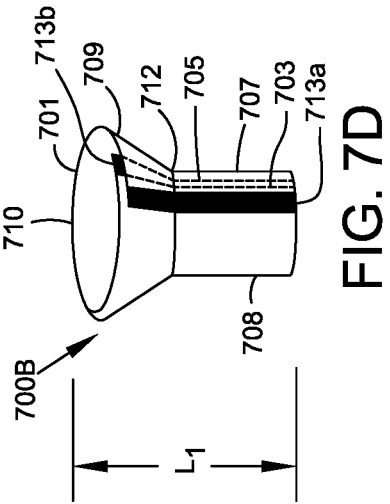
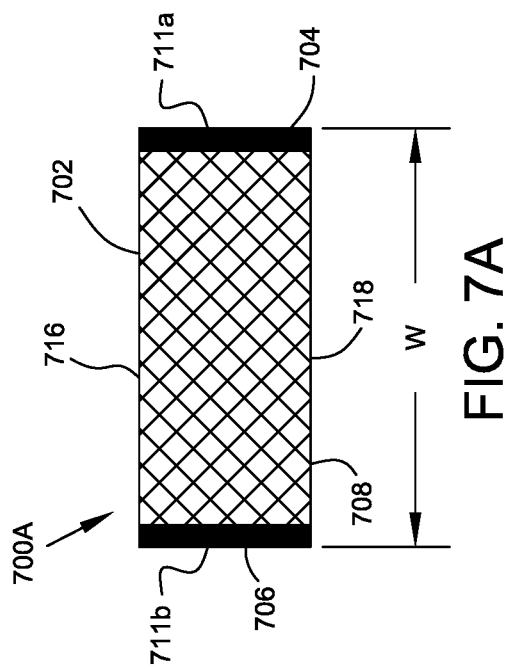
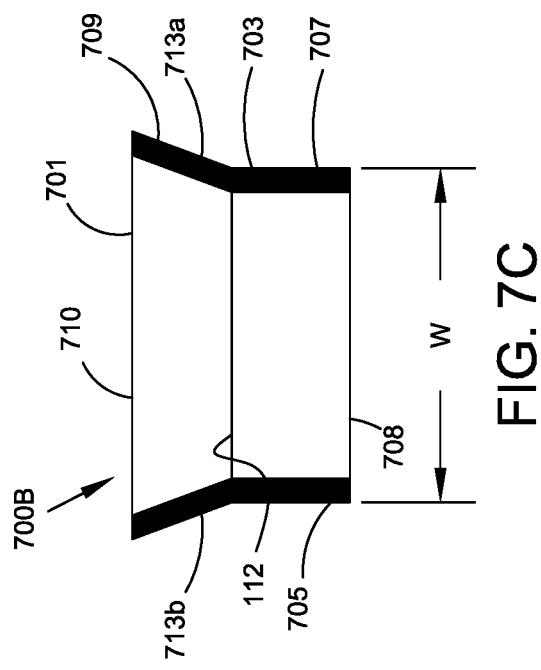

APPARATUS AND METHODS FOR MANAGING A SHAPE OF A JUNCTION BETWEEN A BLADDER AND URETHRA

CROSS-REFERENCE TO RELATED APPLICATION

This application claims the benefit of priority to, U.S. application Ser. No. 17/012,555, filed Sep. 4, 2020, the disclosure of which is expressly incorporated herein by reference to its entirety.

TECHNICAL FIELD

The present disclosure relates generally apparatus and methods for supporting a connection of a bladder and urethra, and more particularly, to apparatus and methods for managing a shape of a junction between the bladder and the urethra to promote the restoration of urinary continence after a prostatectomy.

BACKGROUND

Conventional prostatectomy procedures (e.g., radical prostatectomy or simple prostatectomy) remove all or part of the prostate gland, which is positioned at the base of the bladder and around the urethra. These procedures may use various techniques, including a robot-assisted prostatectomy, an open prostatectomy, or a laparoscopic prostatectomy. During the prostatectomy, at least a portion of the prostate gland and at least a portion of the urethra surrounded by the prostate gland is removed from the patient, resulting in the bladder being detached from the remaining portion of the urethra. Subsequent to removing the prostate gland, the bladder is attached to the remaining portion of the urethra. However, as the length of the urethra is now shortened, connecting the bladder to the urethra results in a strained connection that can cause urinary incontinence post-prostatectomy.

SUMMARY

The present disclosure relates generally to supporting a connection of a bladder and urethra, for example, managing a shape of a junction between the bladder and the urethra to promote urinary continence after a prostatectomy.

In one or more cases, the disclosed technology relates to a device managing a shape of a junction between the bladder and the urethra. In one or more cases, the device comprises an implant having a first portion and a second portion configured to form a hollow interior area within the implant extending along a longitudinal axis thereof. In one or more cases, the first portion and the second portion each configured to form a tubular shape centered about the longitudinal axis. In one or more cases, the first portion is configured to receive a portion of a urethra therein and to be attached thereto. In one or more cases, the second portion is configured to receive an extended portion of a bladder therein and to be attached thereto. In one or more cases, the implant is configured to encase a surgical connection of the urethra and the bladder in the hollow interior area of the implant and to support the operation of one or more sphincter muscles controlling the passage of liquid from the bladder to the urethra.

In one or more cases, the disclosed technology relates to a method of managing a shape of a junction between the bladder and the urethra to control the bladder. In one or more cases, the method comprises inserting a urethra through a hollow interior area of a device. In one or more cases, the hollow interior area extends along a longitudinal axis of the device. In one or more cases, the method includes attaching the urethra to the bladder. In one or more cases, the method includes attaching a first portion of the device to the urethra. In one or more cases, the first portion comprises a tubular shape centered about the longitudinal axis. In one or more cases, the method includes expanding the device longitudinally along the longitudinal axis to a deployed state in which a portion of the bladder extends into the second portion. In one or more cases, the method comprises attaching a second portion of the device to the bladder. In one or more cases, the second portion comprises a tubular shape centered about the longitudinal axis.

The foregoing and other objects, features, and advantages of the disclosure will be apparent from the following more particular descriptions of the embodiments as illustrated in the accompanying drawings.

BRIEF DESCRIPTION OF THE DRAWINGS

The following drawings are illustrative of particular embodiments of the present disclosure and therefore do not limit the scope of the present disclosure. The drawings are not to scale and are intended for use in conjunction with the explanations in the following detailed description.

FIG. 1B is a perspective view of the example support apparatus in a partially expanded state.

FIG. 1C is a perspective view of the example support apparatus in a fully expanded state.

FIG. 7A is a side view of another example support apparatus configured in a first state.

FIG. 7B is a perspective view of the example support apparatus of FIG. 7B configured in a second state.

FIG. 7C is a side view of another example support apparatus configured in a first state.

FIG. 7D is a perspective view of the example support apparatus of FIG. 7C configured in a second state.

DETAILED DESCRIPTION

Figure 1A:
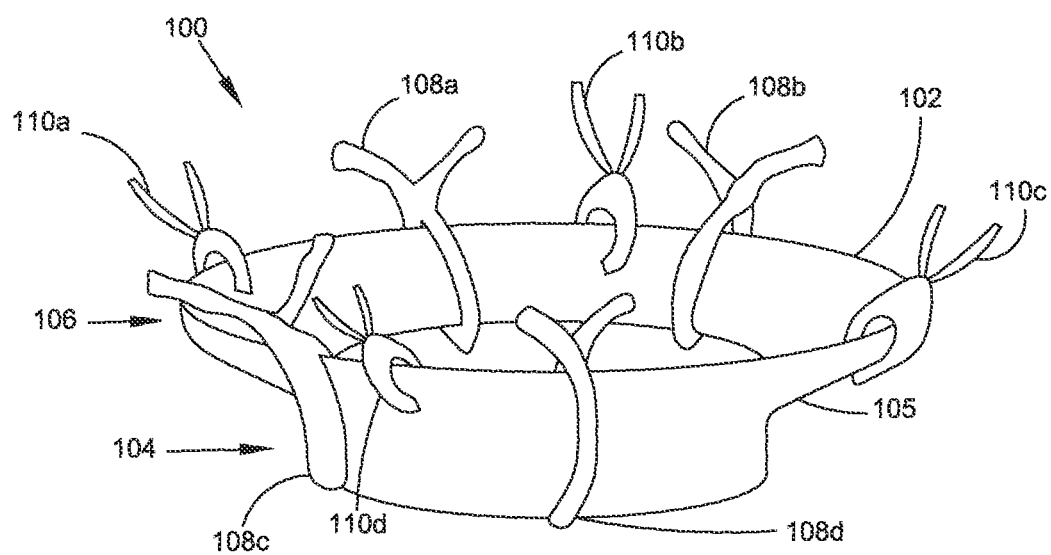
FIG. 1A is a perspective view of an example support apparatus in a compressed state.

The following discussion omits or only briefly describes conventional features of prostatectomies that are apparent to those skilled in the art. It is noted that various embodiments are described in detail with reference to the drawings, in which like reference numerals represent like parts and assemblies throughout the several views. Reference to various embodiments does not limit the scope of the claims attached hereto. Additionally, any examples set forth in this specification are intended to be non-limiting and merely set forth some of the many possible embodiments for the appended claims. Further, particular features described herein can be used in combination with other described features in each of the various possible combinations and permutations.

Unless otherwise specifically defined herein, all terms are to be given their broadest reasonable interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "includes" and/or "including," when used in this specification, specify the presence of stated features, elements, and/or components, but do not preclude the presence or addition of one or more other features, steps, operations, elements, components, and/or groups thereof. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively or operably connected" is such an attachment, coupling or connection that allows the pertinent structures to operate as intended by virtue of that relationship Embodiments of the present disclosure relate generally to supporting a connection of a bladder and urethra, for example, managing a shape of a junction between the bladder and the urethra to promote urinary continence after a prostatectomy. Such apparatus and methods may promote the normal operation of one or more sphincter muscles that control a bladder. For example, such apparatus and methods support the urinary sphincter muscles, which are responsible for retention of urine until volitionary voiding is initiated. Embodiments of support apparatus are described below with reference to FIGS. 1A-7D.

Figure 6A:
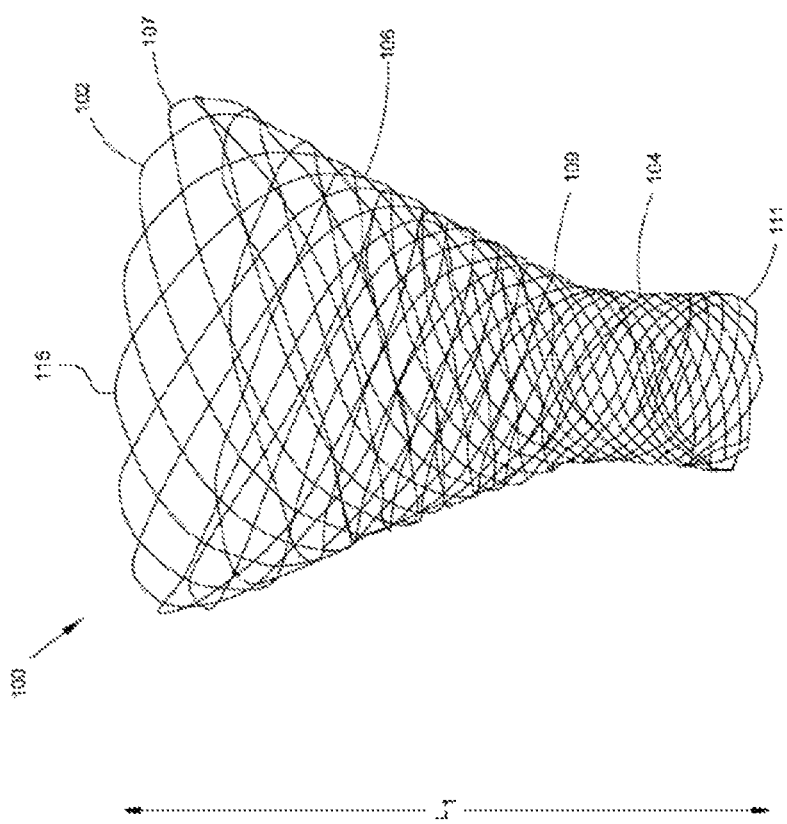
FIG. 6A is a perspective view of an example of the support apparatus of FIGS. 1A-1C.
Figure 6B:
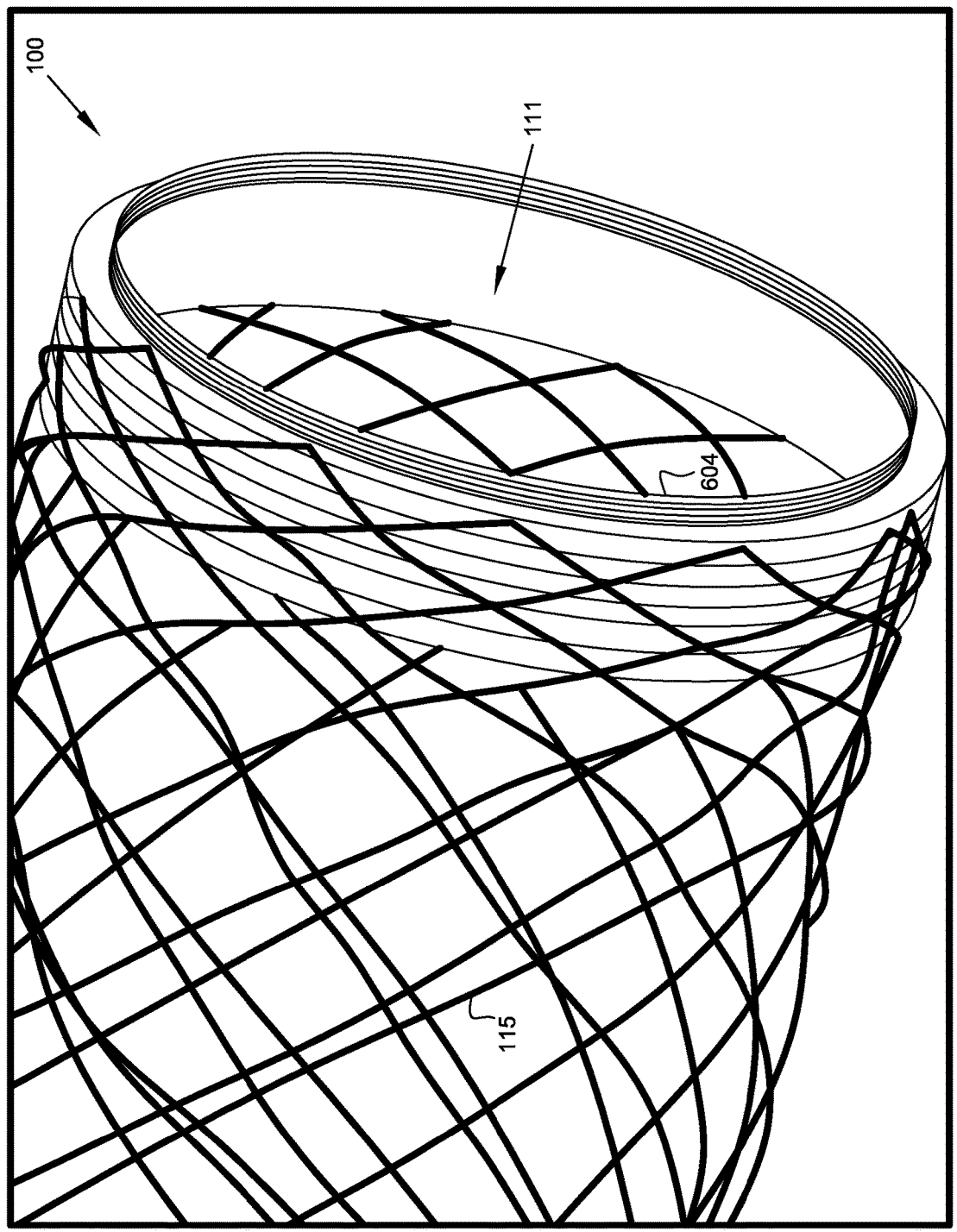
FIG. 6B is a perspective view of a distal end an embodiment of the support apparatus of FIG. 6A.

FIG. 1A is a perspective view of an example support apparatus 100 (hereinafter "apparatus 100"). FIG. 1B is a perspective view of the apparatus 100 in a partially expanded state. FIG. 1C is a perspective view of the apparatus 100 in a fully expanded state. FIG. 6A is a perspective view of the apparatus 100, formed in a braid. FIG. 6B is a perspective view of a flange on a distal end of the apparatus 100.

In one or more embodiments, the apparatus 100 includes an implant 102, one or more compressing members, such as compressing members 108a, 108b, 108c, 108d and compressing members 110a, 110b, 110c, and 110d, and one or more sizing members, such as sizing members 114a, 114b, and 114c. It is noted that FIGS. 1A, 1B, and 1C illustrate the apparatus 100 including the implant 102, compressing members 108a, 108b, 108c, 108d, compressing members 110a, 110b, 110c, and 110d, and sizing members 114a, 114b, and 114c. However, it should be understood that the apparatus 100 may include the implant 102 and none of the aforementioned members, or one or more of the aforementioned members. For example, the apparatus 100 may include the implant 102. In another example, the apparatus 100 may include the implant 102, compressing members 110a, 110b, 110c, and 110d, and sizing members 114a, 114b, and 114c. In yet another example, the apparatus 100 may include the implant 102, compressing members 108a, 108b, 108c, 108d, and compressing members 110a, 110b, 110c, and 110d.

The implant 102 may be a flexible tubular member having a first portion 104 and a second portion 106 forming a hollow interior area within the implant 102. The hollow interior area extends along a longitudinal axis L1 of the implant 102. In one or more cases, the first portion 104 of the implant 102 may be a flexible tubular member having a cylindrical body configured to receive at least a portion of a urethra. In one or more cases, the second portion 106 of the implant 102 may be a flexible tubular member configured to receive at least a portion of a sphincter muscle, such as, but not limited to, a bladder. In some cases, the second portion 106 may taper from a wider end 107 to a narrower end 109 proximal to the first portion 104. The first portion 104 and the second portion 106 may be integrally formed to have a unibody construction.

In one or more cases, the first portion 104 and the second portion 106 may be formed such that the entirety of the implant 102 has a tapered shape, in which a wider end of the implant (e.g., wider end 107 of the second portion 106) is formed on the bladder receiving end and a narrower end (e.g., the distal end 111 of the first portion 104) is formed on the urethra receiving end. In yet one or more other cases, the first portion 104 and second portion 106 may be formed such that the entirety of the implant 102 has a substantially cylindrical shape. In one or more cases, the implant 102 may preferably be formed of a compressible, shape-memory material, such as Nitinol or other types of polymers and biocompatible materials. In one or more other cases, the implant 102 may be formed of a mesh, a braided sheet, or a solid extrusion sized to wrap an anastomosis. In one or more cases, the materials of apparatus 100 may be bioresorbable. Implant 102 may be formed by braiding the compressible, shape-memory material into a braid (e.g., braid 115 illustrated in FIGS. 6A and 6B). In one or more cases, the braid 115 may dilate when compressed, thereby facilitating the placement of the implant 102 in connection with a prostatectomy. In one or more cases in which the implant 100 is attached during a prostatectomy procedure as described herein, the braid 115 may constrict when squeezed along the longitudinal axis L1 of the implant 102, for example, when a patient coughs or moves, thereby ameliorating or preventing urine leakage post prostatectomy. In one or more cases, the material of implant 102 is compatible with antibiotics. Implant 102 may further comprise an antibacterial biomaterial, including, for example, an antibiotic coating. In one or more cases, the materials of the implant 102, may be bioresorbable. The bioresorbable material may be used to mitigate risk of infection and migration. In one or more cases, the bioresorbable material may be configured to resorb over a period to provide mechanical support while the anastomosis heals and may resorb completely once fully healed. In one or more other cases the bioresorbable configuration acts a scaffold for fibrotic tissues to form in a geometry that is favorable for urinary continence without the support of the device after it is fully resorbed. In one or more other cases, the materials of the implant 102 may not be bioresorbable, such that features of the apparatus 100 (e.g., positioning members 113a and 113b illustrated in FIGS. 1B and 1C) may be implemented in a subsequent procedure as described herein. In one or more cases, the end 107 of the second portion 106 and/or the distal end 111 of the first portion 104 may include a flange (e.g., flange 604 illustrated in FIG. 6B) that facilitates suturing the implant 102 to the bladder and urethra, respectively. It is noted that the braid 115 of the implant 102 may be positioned on the outside circumferential surface of the flange 604 as illustrated in FIG. 6B, but it should be understood that the braid 115 of the implant 102 may be positioned on the inner circumferential surface of the flange 604. Further, in one or more cases, the flange 604 may be terminated to create an atraumatic edge that prevents fraying or irritation to adjacent tissues. In one or more cases the termination can be formed with a dipping process. In one or more other cases, the ends of the braid 115 may be heat treated to melt strands of the braid 115 together, thereby forming the flange 604. The ordinary artisan will appreciate that end 107 and/or distal end 111 itself may not need to be sutured to the bladder or urethra, respectively, so long as the implant 102 is sufficiently anchored to the bladder and/or urethra.

When a portion of the bladder is inserted within the second portion 106, the portion of the bladder may be extended and narrowed within the second portion 106. In some cases, the bladder may be further extended through the second portion 106 and into the first portion 104. The extended and narrowed portion of the bladder forms a pseudo-urethra and extends the effective length of urethra, thereby mitigating incontinence. In that way a longer effective length of urethra is provided by the actual urethra together with the portion of the bladder that is extended and narrowed to mimic a prostatic part of the urethra that was removed. That is, the implant 102 encases the surgical connection of the bladder and the urethra in the hollow interior area of the implant 102, and allows a portion of the bladder to function more like the urethra. The implant 102, meanwhile, mitigates competing stresses that an elongated and unconstrained bladder neck places on the sphincter muscle(s) that establish continence. Mitigating such stress using implant 102 may advantageously ameliorate or prevent urinary incontinence post prostatectomy. Further, the implant 102 may manage the geometry of the bladder neck and the urethra acutely. For example, the implant 102 may act as a scaffold for fibrotic tissue (i.e., scar tissue) to form a mechanically sound anastomosis with a favorable geometry (i.e., a greater urethral length).

In one or more cases, the implant 102 may be configured in a compressed state, as shown in FIG. 1A, and in various expanded states, as shown in FIGS. 1B and 1C. One or more compressing members may be removably disposed around the wall 105 of the implant 102, such that the implant 102 is retained in the compressed state until removal of the one or more compressing members. In one or more cases, a compressing member may be surgical thread made of material, such as silk or nylon, and capable of being tied together to compress at least a portion of the implant 102. In one or more other cases, the compressing member may be another type of compressing fastener such as a twist tie or zip tie. For the cases in which the compressing members are removed from the implant 102, the compressing members may be discarded. In some cases, the compressing members may be made of bioresorbable material. The bioresorbable compressing members may provide increased safety, as these bioresorbable compressing members may dissolve if accidently left inside a patient during a procedure.

In one or more cases, a compressing member, such as compressing member 108a, may advantageously facilitate installation of the implant into the body. By retaining the implant in a compressed state, the implant is physically smaller and more manageable during the initial insertion. Controlling the expansion of the implant thereafter beneficially allows for controlled suturing and shaping of the bladder and urethra. Such compressing member may extend along the inner surface of the wall through the hollow of the implant and along the outer surface of the wall 105 of the implant 102, in which the compressing member may be fastened to the implant 102 to compress at least a portion of the implant 102. In some cases, the compressing member may be retained around the entirety of the wall 105 to compress the respective portion of the implant 102. In other cases, the compressing member may be retained around a portion of the wall 105 to compress the respective portion of the implant 102. For example, the compressing members 108a, 108b, 108c, and 108d may be retained around the first portion 104 of the implant 102, thereby compressing the first portion 104 of the implant 102. In another example, compressing members 110a, 110b, 110c, and 110d may be retained around the second portion 106 of the implant 102, thereby compressing the second portion 106 of the implant 102.

By retaining compressing members around certain portions of the implant 102, compressing members may be selectively removed to expand certain portions of the implant 102. For instance, when compressing members 108a, 108b, 108c, and 108d are removed from implant 102, the first portion 104 of the implant 102 may be expanded along the longitudinal axis L1, as illustrated in FIG. 1B. In another instance, when compressing members 110a, 110b, 110c, and 110d are removed from the implant 102, the second portion 106 of the implant 102 may be expanded along the longitudinal axis L1, as illustrated in FIG. 1C. The sequence of removing the compressing members may be selected during installation to control how the implant expands relative to the points of attachment to the bladder or urethra. To deploy the implant 102 or a portion of the implant 102 into an expanded state, the compressing member 102 may be removed by, for example, cutting the compressing member or untying the compressing member. In one or more cases, the compressing members may include a visual identifier to signify the portion of the implant 102 being compressed by the compressing member. For example, the compressing members may be color coded such that each compressing member includes a different color. For instance, compressing members 108a, 108b, 108c, and 108d may be made of a surgical thread having a green color, and compressing members 110a, 110b, 110c, and 110d may be made of a surgical thread having a yellow color.

In one or more cases, the compressing members may be positioned to evenly retain the implant 102 in a compressed state. For example, when four compressing members are implemented, such as compressing members 110a, 110b, 110c, and 110d, the compressing members may be positioned at the 12 o'clock, 3 o'clock, 6 o'clock, and 9 o'clock positions of the implant 102 when viewed from a top view. It is noted that four compressing members are illustrated to compress the first portion 104 and the second portion 106, respectively. However, it should be understood that any number of compressing members may be used to retain the implant 102 in a compressed state. For example, two compressing members may be disposed around the entirety of the wall of the implant 102 at the 3 o'clock and 9 o'clock positions respectively to retain the implant 102 in a compressed state. In another example, two compressing members may be used to retain the first portion 104 in the compressed state, and three compressing members may be used to retain the second portion 106 in the compressed state. It is noted that the compressing members may be optionally included to compress the implant 102. That is, in the alternative to compressing one or more portions of the implant 102, the implant 102 may be initially configured in the expanded state as illustrated in FIG. 1C. Moreover, it is noted that for the cases in which the implant 102 is initially configured in the expanded state, the implant 102 may be subsequently compressed, via one or more compressing members, into a compressed state as illustrated in FIG. 1A prior to or after being implanted in a patient's body. Subsequently, the implant 102 may be deployed into the expanded state, as described herein.

In one or more cases, the one or more sizing members 114a, 114b, and 114c may encircle portions of the wall 105 of the implant 102. In one or more cases, these components may form a zip tie or function as a zip tie. For example, sizing member 114c may encircle the second portion 106, and sizing members 114a and 114b may encircle opposite end portions of the first portion 104, as illustrated in FIG. 1C. In another example, one sizing member may encircle a portion of the wall 105 of the implant 102.

The sizing member, for example sizing member 114a, may be configured to increase and/or decrease the diameter of the wall 105 of the implant 102. By tightening the sizing member, the diameter of the wall 105 decreases, and by loosening the sizing member, the diameter of the wall 105 increases. For example, to decrease the diameter of the second portion 106, the sizing member 114c may be tightened. The sizing member may include a sizing strap, such as strap 116a, 116b, or 116c, and one or more sizing loops, such as sizing loops 118a, 118b, and 118c. The sizing loops may be circumferentially disposed around the outer surface of the wall 105 forming a guide for receiving the sizing strap. For example, the sizing strap 116b may encircle the wall 105 by passing through the sizing loops 118a. By inserting the sizing strap through the one or more sizing loops, the sizing loops 118a may maintain the position of the sizing strap on the wall 105 of the implant 102. In one or more cases, the sizing loop may be formed of the same material as the implant 102. In one or more other cases, the sizing loop may be formed of a surgical thread, in which opposite ends of the sizing loop are fastened to the wall 105, thereby forming a loop (e.g., a through-hole) under the unfastened portion of the sizing loop. The sizing strap may pass through the loop. In one or more cases, the sizing strap may be a zip tie, twist tie, surgical thread, or other like material that can be fastened around the wall 105 of the implant 102. The sizing strap may be bioresorbable. In one or more cases, to size the sizing member, a user (such as but not limited to a physician surgically installing the implant 102) may insert a catheter into the patient and through the urethra, such that the catheter is positioned within the urethra or bladder and one or more of the sizing members. The user may tighten the sizing member until the user receives feedback that the sizing member is snugly fit around the urethra or bladder. For example, while tightening the sizing member, the user may feel increased tension as the diameter of the urethra or bladder is reduced around the catheter.

In one or more cases, the sizing member may include one or more burrs disposed on the sizing member and circumferentially disposed around the wall 105 of the implant 102. The burrs may protrude outward from the sizing member and may temporarily engage and anchor one or more surfaces of the bladder, urethra, or implant. The burrs may advantageously prevent, for example, the implant 102 from sliding along the urethra while the implant 102 is being attached to the urethra. In one or more cases, the sizing member may include loops or suture bands disposed on the sizing member and circumferentially disposed around the wall 105 of the implant 102. A user may pass sutures through the loops or suture bands to facilitate suturing the implant 102 to one or more portions of the urethra and bladder as described herein.

In one or more other cases, the implant 102 does not include a sizing member, but the diameter of the wall 105 is pre-sized to a diameter of a urethra, such that the implant may snugly receive at least a portion of the urethra therein. In yet one or more other cases, the implant 102 is pre-sized to a diameter of the urethra and includes one or more sizing members to make additional adjustments to the diameter of the implant 102.

Figure 3A:
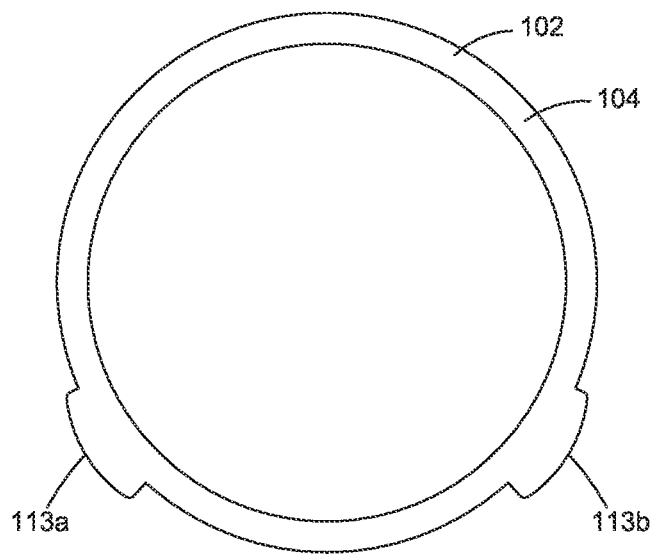
FIG. 3A is a top view of the example support apparatus, in which one or more example inflation balloons are in a deflated state.
Figure 3B:
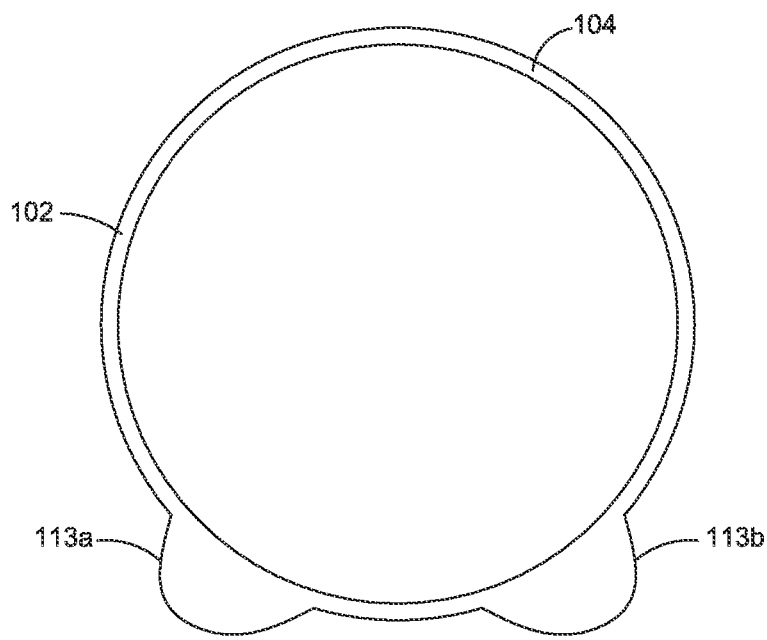
FIG. 3B is a top view of the example support apparatus, in which the one or more example inflation balloons are in an inflated state.

In one or more cases, one or more positioning members, such as positioning members 113a and 113b, may be pre-attached and disposed on an outer surface of the wall 105. The positioning members 113a and 113b each include a balloon, such as balloons 112a and 112b, and a valve, such as valve 120a and 120b. The positioning members 113a and 113b are configured to inflate by inserting a catheter into the respective valve 120a, 120b and inserting a solution, such as a saline solution, into the balloon. By inserting the saline solution or bulking agent into the balloon, the balloon may inflate outwards in a radial direction from the longitudinal axis L1, as illustrated in FIG. 3B. Conversely, by removing the saline solution from the balloon, the balloon may deflate inwards in the radial direction from the longitudinal axis L1, as illustrated in FIG. 3A. During the prostatectomy procedure, the implant 102 may be positioned such that when the balloons 112a and 112b are inflated post-prostatectomy, the balloons 112a and 112b may press against a portion of the patient's body causing the bladder neck to lift upwards as one or both of the balloons 112a and 112b are inflated. In one or more cases, all or a portion of the positioning member, such as the valve 120a of positioning member 113a, may be formed out of radio-opaque material or radiolucent material, such that the positioning member or a portion thereof may be visible in certain imaging procedures, such as, but not limited to a fluoroscopy. For example, using image guidance, such as viewing an x-ray, a user may guide the catheter to the radio-opaque or radiolucent valve 120a to inflate or deflate the balloon 112a.

In one or more other cases, the one or more positioning members, such as positioning members 113a and 113b, may be coupled to the outer surface of the wall 105 after one or more portions of the implant 102 is configured in an expanded state. For instance, during the prostatectomy procedure, the first portion 104 is expanded and secured to at least a portion of the urethra; a user may position the positioning members 113a and 113b to the portion of the patient's body as described herein; and the user may couple the positioning members 113a and 113b to the outer surface of the wall 105. The user may couple the positioning members 113a and 113b to the wall 105 via adhesive, suturing, or other like coupling means. In yet one or more other cases, during a subsequent procedure (i.e., post-prostatectomy), a user may position and couple the positioning members 113a and 113b to the outer surface of the wall 105 as described herein. Moreover, during the post-prostatectomy procedure, the user may inflate the positioning members 113a and 113b as described herein.

Figure 2A:
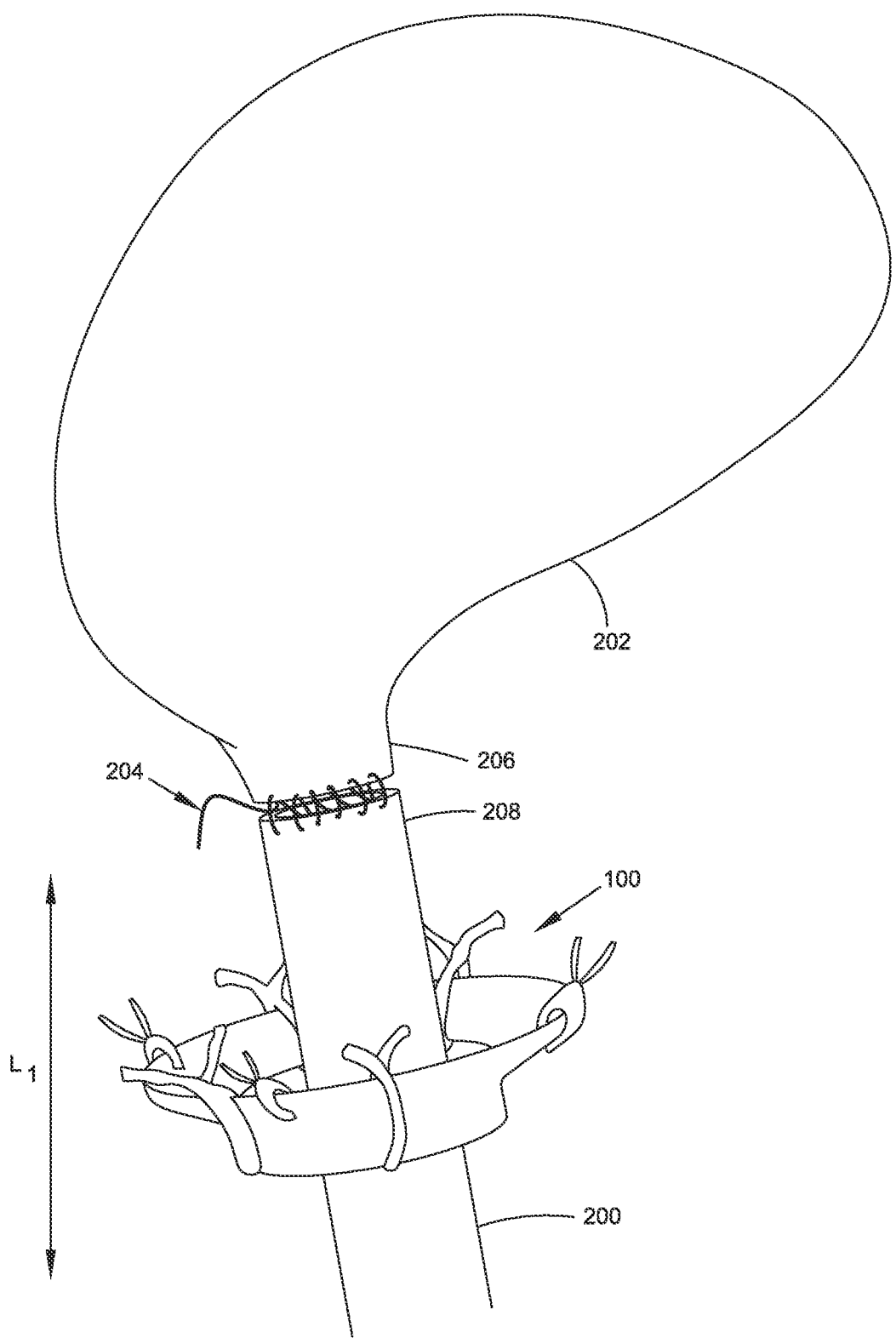
FIG. 2A illustrates the example support apparatus inserted over a sphincter muscle.
Figure 2B:
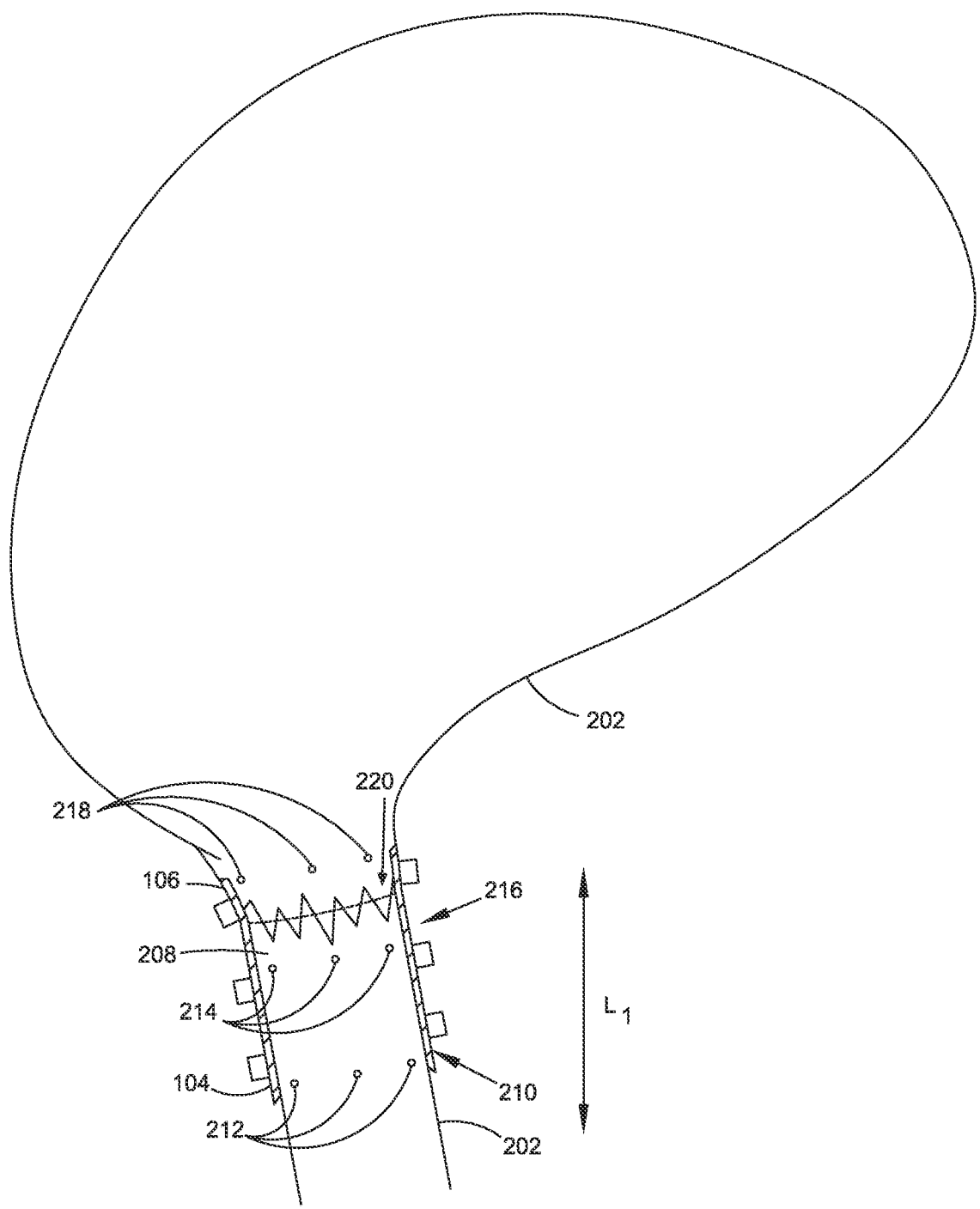
FIG. 2B illustrates a cross-sectional view of the example support apparatus attached to the one or more example sphincter muscles.

During a prostatectomy, a user may remove all or a portion of the prostate gland. Having removed all or a portion of the prostate gland, the user inserts a detached urethra 200 through the apparatus 100, which is configured in the compressed state. The user may suture an end portion 206 of the bladder 202 to an end portion 208 of the urethra 200, via, for example, a surgical suture 204, as illustrated in FIG. 2A. In one or more cases, having attached the urethra 200 and the bladder 202, the apparatus 100 may be attached to the urethra 200 and the bladder 202 in a variety of steps and in various locations of the urethra 200 and the bladder 202.

For instance, the user may remove one or more compressing members, such as compressing members 108a, 108b, 108c, and 108d, to expand the first portion 104 of the apparatus 100 in a direction of the longitudinal axis L1. For the cases in which the apparatus 100 includes pre-attached positioning members 113a and 113b, the user may position the positioning members 113a and 113b to be inflated against a body post-prostatectomy, as discussed herein. The user may then suture the distal end 210 of the first portion 104 at various points, such as point 212, around the urethra 200, thereby securing the position of the positioning members. In some cases, the user may suture the distal end 210 of the first portion 104 on or as close to pelvic floor as possible. It is noted that the user may also remove the compressing members 108a, 108b, 108c, and 108d after suturing the distal end 210 of the apparatus 100 to the urethra 200. In some cases, the user may set the diameter of the wall 105 via the one or more sizing members 114a and 114b as discussed herein, thereby setting the diameter of the urethra 200. The user may suture the proximal end 216 of the first portion 104 at various points, such as points 214, on the end portion 208 of the urethra 200. The user may then remove compressing members 110a, 110b, 110c, and 110d to expand the second portion 106 in the direction of the longitudinal axis L1. It is noted that the second portion 106 may be expanded before positioning the positioning members 113a and 113b; before suturing the distal end 210 of the first portion 104 to the urethra 200; before setting the diameter of the wall 105; or before suturing the proximal end 216 of the first portion 104 to the end portion 208 of the urethra 200.

Having sutured the proximal end 216 of the first portion 104 to the end portion 208 of the urethra 200, the user may suture a proximal end portion 220 of the bladder 202 to the second portion 106 at various suture points, such as suture points 218. When suturing the proximal end portion 220 to the second portion 106, the proximal end portion 220 of the bladder 202 may extend into and narrow within the second portion 106. Further, the user may set the diameter of the wall 105 of the second portion 106 to further narrow the proximal end portion 220 within the second portion 106. The apparatus 100 extends the effective length of the urethra 200 via the extended and narrowed portion of the bladder, as such, incontinence after the prostatectomy is mitigated or reduced. For the cases in which the positioning members 113a and 113b are not pre-attached, the positioning members 113a and 113b may positioned and coupled to the wall 105 after expanding the first portion 104, after expanding the second portion 106, or after suturing the proximal end portion 220 to the second portion 106. The positioning members 113a and 113b may be positioned in a deflated stated.

It is noted that the procedure described herein discusses removing the compressing members to expand the implant 102. However, for cases in which the implant 102 does not include the compressing members and the implant 102 is initially configured in the expanded state, the user inserts a detached urethra 200 through the apparatus 100, attaches the urethra 200 and the bladder 202 as described herein, and attaches the portions of the apparatus 100 to the respective portions of the urethra 200 and bladder 202 as described herein.

For the cases in which the patient fails to regain continence or begins to develop symptoms of incontinence post-prostatectomy, in a subsequent procedure, the user may insert a catheter into the patient, and guide the catheter to the one or more positioning members 113a and 113b, as described herein. The user may insert the catheter into the valves 120a and 120b and inflate the balloons 112a and 112b. As the balloons 112a and 112b are inflated, the balloons contact and press against a portion of the patient, thereby causing the apparatus 100 and the bladder neck to lift upwards and reestablish continence. In addition to or as an alternative to inflating the balloons 112a and 112b, the user may tighten one or more of the sizing members 114a, 114b, and 114c. For the cases in which the positioning members 113a and 113b were not coupled to the implant 102 during the prostatectomy procedure, during a subsequent procedure, the user may invasively position and couple the positioning members 113a and 113b to the outer surface of the wall 105 as described herein. Having coupled the positioning members to the implant 102, the user may inflate the balloons 112 and 112b as described herein.

In one or more other cases in which all or a portion of the prostate gland is removed, the user may alternatively insert the detached urethra 200 through the apparatus 100, which is configured in the compressed state. The user may suture the distal end 210 of the first portion 104 to the urethra 200, and suture the end portion 206 of the bladder 202 to the end portion 208 of the urethra 200. The user may subsequently attach the remaining portions of the apparatus 100 as described herein.

For other cases in which most or all of the urethra 200 is removed during the prostatectomy, the user may suture the distal end 210 of the first portion 104 on or close to the pelvic floor, expand and position the apparatus 100 as described herein, and suture the proximal end portion 220 to the second portion 106 as described herein. In such cases, as the urethra 200 is not long enough to attach the proximal end 216 of the first portion 104, the user may preferably not suture the proximal end 216 of the first portion 104. In one or more other cases in which the second portion 106 does not extend over the bladder 202, the user may suture the distal end 210 of the first portion 104 to the urethra 200. In some additional cases in which the second portion 106 does not extend over the bladder 202, the user may also suture the proximal end 216 of the first portion 104 at various points, such as points 214, on the end portion 208 of the urethra 200.

It is noted that the apparatus 100 illustrated in FIGS. 6A and 6B includes one or more of the same or similar features as those described with respect to apparatus 100 illustrated in FIGS. 1A-3B. For example, the apparatus 100 of FIGS. 6A and 6B includes an embodiment of implant 102. In another example, the apparatus 100 of FIGS. 6A and 6B includes embodiments of implant 102 with one or more of the compressing members, sizing members, and positioning members and other embodiments described with respect to FIGS. 1A-3B. Accordingly, a description of such features is not repeated.

Figure 4:
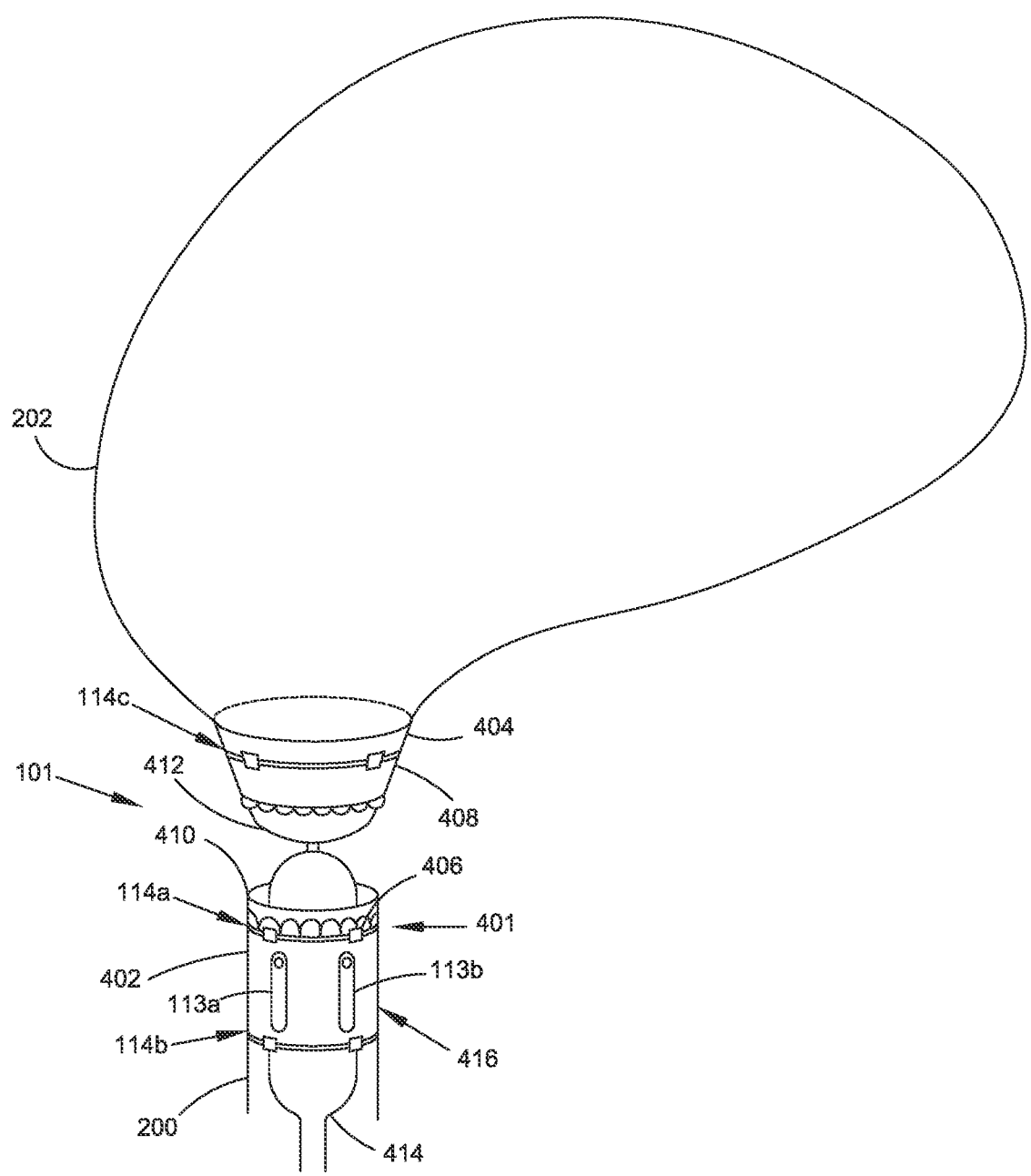
FIG. 4 is a perspective view of another example support apparatus.

FIG. 4 is a perspective view of another example support apparatus 101 (hereinafter "apparatus 101").

In one or more embodiments, the apparatus 101 includes an implant 401 having a first portion 402 and a second portion 404, one or more sizing members, such as sizing members 114*a*, 114*b*, and 114*c*, and one or more positioning members, such as positioning members 113*a* and 113*b*. It is noted that the sizing members 114*a*, 114*b*, and 114*c* and the positioning members 113*a* and 113*b* of apparatus 101 include the same or similar features as the sizing members 114*a*, 114*b*, and 114*c* and the positioning members 113*a* and 113*b* of apparatus 100, as such the description of these members is not repeated.

In one or more cases, the first portion 402 is a cylindrically tubular member that includes a flange 406 on the proximal end of the first portion 402, and the second portion 404 is a tubular member having a funnel-like shape that includes a flange 408 on a proximal end of the second portion 404. The flanges 406 and 408 are formed of a rigid or semi-rigid material that facilitate suturing together the first portion 402 and the second portion 404.

During a prostatectomy, the user may remove all or a portion of the prostate gland. Having removed all or a portion of the prostate gland, the user inserts a detached urethra 200 through the first portion 402. In one or more cases, the first portion 402 may be configured in a compressed state via one or more compressing members, such as compressing members 108*a*, 108*b*, 108*c*, and 108*d*. In some cases, the user may remove the compressing members after suturing a distal end portion 416 of the first portion 402 to the urethra 200. In other cases, the user may remove the compressing members before suturing a distal end portion 416 of the first portion 402 to the urethra 200. The user may suture the distal end portion 416 of the first portion 402 to the urethra 200 such that a portion of the proximal end 410 of the urethra 200 extends beyond the proximal end 406 of the first portion 402. The user may insert a catheter 414 through the urethra 200 and position the catheter 414 within the first portion 402, such that the shape of the urethra 200 is maintained or substantially maintained when attaching the bladder 202 to the urethra 200.

The user may insert the second portion 404 over the proximal end 412 of the bladder 202, and suture the second portion 404 to the bladder 202 such that a portion of the proximal end 412 of the bladder 202 extends beyond the proximal end 408 of the second portion 404. The user may attach the bladder 202 to the urethra 200 by suturing the portions of the bladder 202 and the urethra, which extend beyond the proximal ends 406 and 408 respectively, to one another. Having attached the bladder 202 and the urethra 200, the user may further extend the proximal end 406 of the first portion 402 and/or the proximal end 408 of the second portion 404 towards one another. The user may then suture the first portion 402 and the second portion 404 to one another. Subsequently, the user may remove the catheter 414. In a same or similar manner as the apparatus 100, the apparatus 101 extends the effective length of the urethra 200 via the extended and narrowed portion of the bladder, and as such, incontinence after the prostatectomy may be further mitigated or reduced.

Figure 5B:
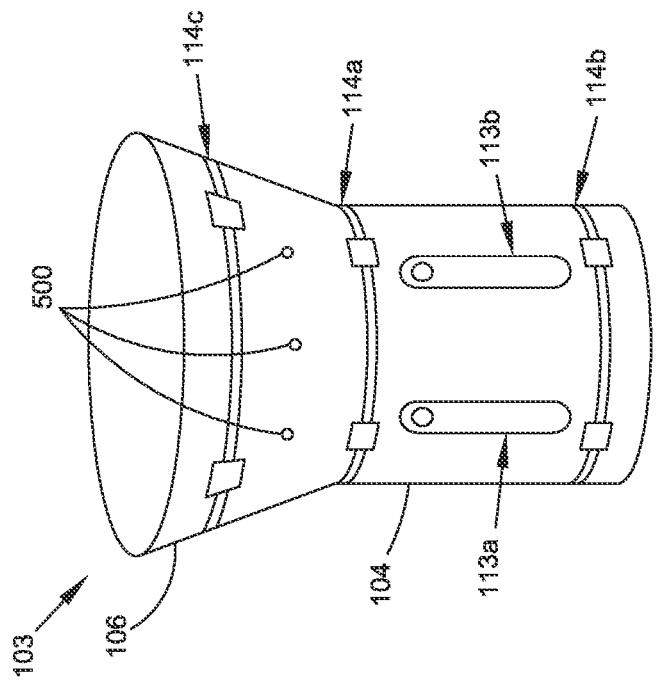
FIG. 5B is a perspective view of the example support apparatus of FIG. 5A in an unfolded state.
Figure 5A:
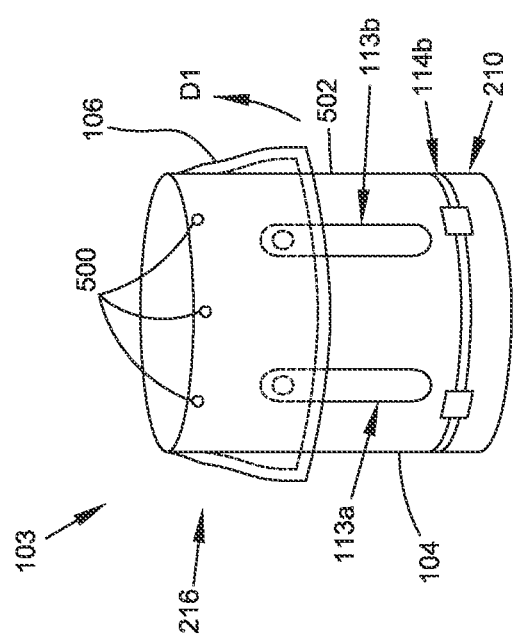
FIG. 5A is a perspective view of another example support apparatus in a folded state.

FIG. 5A is a perspective view of another example support apparatus 103 (hereinafter "apparatus 103") in a folded state. FIG. 5B is a perspective view of the apparatus 103 in an unfolded state.

In one or more embodiments, the apparatus 103 includes an implant 502, one or more sizing members, such as sizing members 114*a*, 114*b*, and 114*c*, and one or more positioning members, such as positioning members 113*a* and 113*b*. It is noted that the sizing members 114*a*, 114*b*, and 114*c* and the positioning members 113*a* and 113*b* of apparatus 103 include the same or similar features as the sizing members 114*a*, 114*b*, and 114*c* and the positioning members 113*a* and 113*b* of apparatus 100, as such the description of these members is not repeated. Further, one or more compressing members, such as compressing members 108*a*, 108*b*, 108*c*, and 108*d*, may be removably disposed around at least a portion of the first portion 104. The one or more compressing members may retain the first portion 104 in a partially compressed state such that a portion of the first portion 104 is not covered by the folded second portion 106 and can be sutured to the urethra 202.

In one or more cases, the implant 502 includes the first portion 104 and the second portion 106. It is noted that the first portion 104 and the second portion 106 of implant 502 include the same or similar features as the first portion 104 and the second portion 106 of implant 102, as such a description of these features is not repeated. The implant 502 is distinguishable from implant 102 in that the implant 502 is initially configured in a folded state, as illustrated in FIG. 5A. In one or more cases, the second portion 106 is folded outwards and over at least a portion of the first portion 104 in the folded state.

During a prostatectomy, the user may remove all or a portion of the prostate gland. Having removed all or a portion of the prostate gland, the user inserts a detached urethra 200 through the first portion 104 and folded second portion 106 of the implant 503. In some cases, the user may suture the distal end 210 of the first portion 104 to the urethra 200, and, before or after suturing the distal end 210 to the urethra 200, the user may suture the proximal end 216 of the first portion 104 from the inside of the implant 502 to the urethra 200 at one or more suture points, such as suture points 500. The user may suture the bladder 202 to the urethra 200 as described herein. It is noted that the user may suture the bladder 202 to the urethra 200 before suturing the distal end 210 of the first portion 104 to the urethra 200 and suturing the proximal end 216 to the urethra 200; in between suturing the distal end 210 of the first portion 104 to the urethra 200 and suturing the proximal end 216 to the urethra 200; or after suturing the distal end 210 of the first portion 104 to the urethra 200 and suturing the proximal end 216 to the urethra 200. Subsequent to suturing the first portion 104 to the urethra 200 and suturing the bladder 202 and the urethra 200, the user may unfold the second portion 106 in a direction D1 into the unfolded state as shown in FIG. 5B. The user may suture the second portion 106 to the bladder 202 as described herein.

FIG. 7A is a side view of an example support apparatus (hereinafter "apparatus 700A") configured in a first state. FIG. 7B is a perspective view of the apparatus 700A configured in a second state.

In one or more embodiments, apparatus 700A includes implant 702 having features described for other embodiments herein. Following the teaching of this specification, the ordinary artisan will appreciate multiple combinations of features are available. For example, implant 702 may include one or more compressing members, such as compressing members 108*a*, 108*b*, 108*c*, 108*d* and compressing members 110*a*, 110*b*, 110*c*, and 110*d*, one or more sizing members, such as sizing members 114*a*, 114*b*, and 114*c*, and one or more positioning members, such as positioning members 113a and 113b. It should be understood that apparatus 700A may include implant 702 and none of the aforementioned members, or one or more of the aforementioned members. For example, apparatus 700A may include implant 702 alone. In another example, the apparatus 700A may include implant 702 and sizing members 114a, 114b, and 114c. One or more compressing members, such as compressing members 108a, 108b, 108c, 108d and compressing members 110a, 110b, 110c, and 110d, one or more sizing members, such as sizing members 114a, 114b, and 114c, and one or more positioning members, such as positioning members 113a and 113b, may be used for apparatus 700A with the same or similar features as those described with respect to apparatus 100 illustrated in FIGS. 1A-3B. Accordingly, a description of such features is not repeated.

The implant 702 may be a flexible sheet 708 that is adapted to form (such as by rolling, wrapping, compressing or the like) a tubular shape or partially tubular shape, such as a U-shape, having an interior area within implant 702 for a urethra and/or bladder. It should be understood herein that a tubular or partially tubular shape encompasses geometries defined by wrapping a surface around (wholly or partially) an axis passing through the urethra and bladder. For example, in a first state, as illustrated in FIG. 7A, flexible sheet 708 may be disposed in an open state that may be, for example, flat or substantially flat. It should be understood that the first state need not be a sheet. The first state may be curved with an opening sufficient to allow securing implant 702 around an already-connected urethra-bladder junction. In a second state, as illustrated in FIG. 7B, the flexible sheet 708 is wrapped, crimped, clamped, rolled or otherwise formed into a tubular shape having a hollow interior area within the implant 702. That is, the implant 702 may be positioned by wrapping the anastomosed bladder and urethra, and subsequently stitching into a tubular or mostly tubular geometry of the implant 702 and one or more portions of the anastomosed bladder and urethra.

The tubular shape of the second state is preferably closed (e.g., to completely surround a urethra and bladder), but need not be. For example, in the alternative to overlapping the side portions 704 and 706 as illustrated in FIG. 7B, the flexible sheet 708 may be wrapped partially around the area of the surgical connection between the urethra and bladder forming a partially tubular shape, such that a portion of the urethra and bladder remain unwrapped. That is, the tubular shape may be formed by the placement of sutures securing the edges of the device. For instance, the flexible sheet 708 may be wrapped at least fifty percent (50%) around the surgical connection between the urethra and bladder. The partially wrapped flexible sheet 708 may be attached to the urethra and/or bladder by suturing the partially wrapped flexible sheet 708 to the urethra and/or bladder at a variety of points and in at a variety of patterns. For example, top and bottom corner areas of side portions 704 and 706 may be sutured to the respective areas of the urethra and bladder. In another example, the side portions 704 and 706 may be laced together by suturing one side portion of flexible sheet 708 to the other side portion flexible sheet 708, or by suturing one side portion of flexible sheet 708 and portions of the urethra and/or bladder to the other side portion flexible sheet 708 and other portions of the urethra and/or bladder. In yet another example, the side portions 704 and 706 may be sutured together. While suturing the side portions 704 and 706 together the sutures may also pass through one or more portions of the urethra and/or bladder, thereby further securing the implant 702 to the anastomosed bladder and urethra.

The interior area extends along a longitudinal axis L1 of implant 702. In one or more cases, an end portion, such as end portion 716, of implant 702 is configured to encircle and receive at least a portion of a urethra. In one or more cases, an end portion, such as end portion 718, of implant 702 is configured to encircle and receive at least a portion of a sphincter muscle of, for example, a bladder. In one or more cases, the width (W) along flexible sheet 708 may be pre-sized to form the hollow interior area having a specified diameter (D). In one or more cases, the width (W) of the flexible sheet 708 may be greater than the diameter (D) necessary to wrap around and receive at least a portion of a urethra and/or at least a portion of a sphincter muscle, thereby allowing a user to cut flexible sheet 708 to a desired width before or during an operation, such as a prostatectomy. In one or more other cases, flexible sheet 708 may have a trapezoidal shape in the first state, such that when flexible sheet 708 is configured in the second state, the entirety of implant 702 has a tapered shape. In such cases, the wider end (e.g., end portion 716) is formed on the bladder receiving end and a narrow end (e.g., end portion 718) is formed on the urethra receiving end.

In one or more cases, implant 702 may preferably be formed of a compressible, shape-memory material, such as Nitinol or other types of polymers and biocompatible materials. In some cases, implant 702 may be braided into flexible sheet 708. In one or more cases, the material of implant 702 is compatible with antibiotics. Implant 702 may further comprise an antibacterial biomaterial, including, for example, an antibiotic coating. Implant 702 may be made partially or completely of bioresorbable material.

In one or more cases, flexible sheet 708 includes one or more reinforcement members, such as reinforcement members 711a and 711b that facilitates suturing implant 702 to a bladder and urethra, respectively. In some cases, reinforcement members 711a and 711b are positioned on respective side portions, such as side portion 704 and side portion 706. For example, reinforcement member 711a may be positioned on an edge of side portion 704. In some cases, reinforcement members 711a and 711b may extend the entire length of the respective side portions 704 and 706 of implant 702. In other cases, reinforcement members 711a and 711b may be intermittently disposed along the length of the respective side portions 704 and 706 of the implant 702. For example, reinforcement members 711a may be positioned at the top and bottom of side portion 704 of implant 702. In one or more cases, flexible sheet 708 includes one reinforcement member positioned on either side portions 704 and 706. In one or more other cases, flexible sheet 708 does not include a reinforcement member. Alternatively, in one or more cases, flexible sheet 708 includes loops, such as eyelets, or suture bands disposed on one or more portions of flexible sheet 708, such as, side portions 704 and 706. A user may pass sutures through the loops or suture bands to facilitate suturing implant 702 to one or more portions of an urethra and bladder as described herein. It should be understood that the flexible sheet 708 may include a combination of reinforcement members, loops, and suture bands. For example, the flexible sheet 708 may include reinforcement member 711a on side portion 704, and may include eyelets position along side portion 706. The reinforcement members 711a and 711b may be formed via a dipping process or by heat treating portions of the flexible sheet 708 to melt portions of the flexible sheet 708 together, thereby forming the reinforcement members 711a and 711b.

During a prostatectomy, a user may remove all or a portion of the prostate gland. Having removed all or a portion of the prostate gland, in some cases, the user may form and secure the apparatus 700A into a tubular shape, and implant apparatus 700A in a same or similar manner, as discussed with respect to apparatus 100. Accordingly, a description of such processes is not repeated. The first and second states described for apparatus 700A allow advantageous flexibility in the procedures used for manufacture, distribution and storage of apparatus 700A. For example, apparatus 700A may be manufactured, distributed and stored in the first state. The first and second states also allow advantageous flexibility in the surgical procedures used with apparatus 700A. For example, a surgeon may suture the urethra and bladder together first, insert the apparatus 700A into the body in the first state, wrap apparatus 700A around the sutured urethra and bladder into the second state.

In one or more other cases, having removed all or a portion of the prostate gland, the user may suture an end portion 206 of bladder 202 to an end portion 208 of urethra 200, via, for example, a surgical suture 204, as illustrated in FIG. 2A. A user may subsequently suture a side portion, such as side portion 704, to portions of bladder 202 and/or urethra 200. In some cases, the user may suture a respective reinforcement member, such as reinforcement member 711a to portions of bladder 202 and/or urethra 200. Having fastened a side portion to bladder 202 and/or urethra 200, the user may wrap implant 702 around bladder 202 and/or urethra 200, such that one side portion, such as side portion 706, overlaps a portion of an opposite side portion, such as side portion 704. The user may pull and wrap side portion 706 over side portion 704 until the implant 702 is snugly fit around the urethra and/or bladder. The user may receive feedback that the implant is snugly fit. For example, while pulling and wrapping side portion 706 over side portion 704, the user may feel increased tension as the diameter of the urethra or bladder is reduced around a catheter that has been inserted through the urethra and bladder. The user may fasten side portion 706 to side portion 704 by suturing the reinforcement member 711b of side portion 706 to one or more portions of side portion 704, and/or to one or more portions of the urethra and bladder. In some cases, the user may fasten side portion 706 to only side portion 704. In other cases, the user may fasten side portion 706 to one or more of side portion 704, urethra, and bladder. In one or more cases, the user may cut off any excess length of flexible sheet 708.

In one or more other cases, the apparatus 700A may be implanted around the urethra and/or bladder in a restorative procedure. For example, a patient may have previously undergone a prostatectomy, in which a portion or all of the prostate was removed and the anastomosis is healed; however, the patient fails to regain continence or begins to develop symptoms of incontinence post-prostatectomy. In a subsequent procedure, the user may implant the apparatus 700A by wrapping the bladder neck and urethra junction with the device and securing in position with sutures. In some cases, the user may suture reinforcement members 711a and 711b to portions of bladder 202 and/or urethra 200. Having fastened a side portion to bladder 202 and/or urethra 200, the user may wrap implant 702 around bladder 202 and/or urethra 200, such that one side portion, such as side portion 706, can be attached to the opposite side portion, such as side portion 704 via sutures. In some instances, the side portions may overlap to form a tube The user may pull and wrap side portion 706 over side portion 704 until the implant 702 is snugly fit around the urethra and/or bladder. The user may receive feedback that the implant is snugly fit. For example, while pulling and wrapping side portion 706 over side portion 704, the user may feel increased tension as the diameter of the urethra or bladder is reduced around a catheter that has been inserted through the urethra and bladder. The user may fasten side portion 706 to side portion 704 by suturing side portion 706 to one or more portions of side portion 704, such as loops suture bands, or reinforcement members. In some cases, the user may fasten side portion 706 to only side portion 704. In other cases, the user may fasten side portion 706 to one or more of side portion 704, urethra, and bladder. In one or more cases, the user may cut off any excess length of flexible sheet 708.

FIG. 7C is a side view of another example support apparatus (hereinafter "apparatus 700B") configured in a first state. FIG. 7D is a perspective view of apparatus 700B configured in a second state. Features described for the other embodiments herein may be applied to the embodiments shown in FIGS. 7C and 7D.

In one or more embodiments, apparatus 700B includes implant 701 having features described for other embodiments herein. Following the teaching of this specification, the ordinary artisan will appreciate multiple combinations of features available. For example, implant 701 may include one or more compressing members, such as compressing members 108a, 108b, 108c, 108d and compressing members 110a, 110b, 110c, and 110d, one or more sizing members, such as sizing members 114a, 114b, and 114c, and one or more positioning members, such as positioning members 113a and 113b. It should be understood that the apparatus 700B may include implant 701 and none of the aforementioned members, or one or more of the aforementioned members. For example, apparatus 700B may include implant 701 alone. In another example, apparatus 700B may include implant 701 and sizing members 114a, 114b, and 114c. The one or more compressing members, such as compressing members 108a, 108b, 108c, 108d and compressing members 110a, 110b, 110c, and 110d, one or more sizing members, such as sizing members 114a, 114b, and 114c, and one or more positioning members, such as positioning members 113a and 113b, may be used for apparatus 700B with the same or similar features as those described with respect to apparatus 100 illustrated in FIGS. 1A-3B. Accordingly, a description of such features is not repeated.

Implant 701 may be a flexible sheet 708 having a first portion 707 and a second portion 709 adapted to be form (such as by rolling, wrapping, compressing, or the like) a hollow interior area within implant 701 for a urethra and/or bladder. The description herein of flexible sheet 708 of FIGS. 7A and 7B is equally applicable to FIGS. 7C and 76D and thus will not be repeated in full. The hollow interior area may extend along a longitudinal axis L1 of implant 701. In one or more cases, first portion 707 of flexible sheet 708 may have a rectangular shape in a first state as illustrated in FIG. 7C, and may have a tubular shape when configured in a second state as illustrated in FIG. 7D (i.e., when the side portion 705 overlaps the side portion 703). The tubular shape may be closed (shown in FIG. 7D) or partially closed (not shown) in the second state. In one or more cases, second portion 709 may have a trapezoidal shape in a first state, and when configured in the second state, second portion 709 may form a tubular member that tapers from a wider end 710 to a narrower end 712 proximal to first portion 707. In one or more cases, flexible sheet 708 of implant 701 includes reinforcement members 713a and 713b. Reinforcement members 713a and 713b may include the same or similar features as reinforcement members 711a and 711b, and a description of such features is not repeated. Reinforcement members 713a and 713b of implant 701 are distinguishable from reinforcement members 711*a* and 711*b* of implant 702 in that the reinforcement members 713*a* and 713*b* may be formed in a shape of the respective side portions 703 (i.e., side portions 707 and 709) of implant 701. For example, reinforcement member 713*a* may extend in the longitudinal direction L1 of implant 701 along side portion 707, and may extend at an outward angle from longitudinal direction L1 of implant 701 along side portion 709.

Apparatus 700B may be implanted during a prostatectomy or restorative procedure in a same or similar manner as apparatus 700A. Accordingly, a description of such processes is not repeated.

The apparatus, implants, components, sutures and other features described herein with respect to FIGS. 1-7D may be made completely or partially of bioresorbable materials, such that the implant may degrade safely in the body over time. A bioresorbable implant may provide necessary support after a new surgical procedure, such as a prostatectomy, but the need for that support may not be necessary at later periods after recovery. For example, tissue growth may obviate the need for the implant, or one or more components of the implant, over time. In particular, embodiments of the implants described above may include a bioresorbable braid, where the braid promotes and supports tissue growth. Being bioresorbable, the braid will degrade safely in situ without need of a removal procedure.

It is noted that the user may perform the procedures described herein manually or robot-assisted, such as with a robotic surgical system like the Da Vinci™ surgical system. It should also be understood that although three suture points are illustrated for suturing a portion of the implant 102 to respective portions of the urethra and bladder, it should be understood that any number of sutures and suture points may be used to fasten the implant to the urethra and bladder. Moreover, the embodiments discussed herein are directed to prostatectomy procedures; however, it should be understood that the apparatus and methods described herein may be applicable to other procedures that involve surgically connecting body parts, such as veins or arteries to respective organs.

As used herein, the term "about" in reference to a numerical value means the numerical value or plus or minus 15% of the numerical value of the number with which it is being used.

The various embodiments described above are provided by way of illustration only and should not be construed to limit the claims attached hereto. Those skilled in the art will readily recognize various modifications and changes that may be made without following the example embodiments and applications illustrated and described herein, and without departing from the spirit and scope of the following claims.

What is claimed is:

1. A device for mitigating urinary incontinence post prostatectomy, the device comprising:
   an implant having a first portion and a second portion, wherein the first and second portions are configured to form a hollow interior area within the implant extending along a longitudinal axis thereof, wherein:
      the first portion and the second portion are each configured to form a tubular shaped wall centered about the longitudinal axis,
      the first portion is configured to receive a portion of a urethra therein and to be secured thereto,
      the second portion is configured to receive an extended portion of a bladder therein and to be secured thereto, and
      the implant is configured to encase a surgical connection of the urethra and the bladder in the hollow interior area of the implant; and
   wherein the device is further configured:
   to lengthen the extended portion of the bladder along the longitudinal axis by extending and narrowing the extended portion of the bladder within the hollow interior area of the device to increase effective urethral length sufficient to mitigate stress that the bladder places on one or more sphincter muscles controlling passage of liquid from the bladder to the urethra to thereby mitigate incontinence.

2. The device of claim 1, wherein the second portion has a tapered shape about the longitudinal axis that tapers outward from a first end of the second portion to a second end of the second portion, the second end being wider than the first end.

3. The device of claim 1, wherein the device is configured to extend and narrow the extended portion of the bladder through the second portion of the implant and into the first portion of the implant, further increasing effective urethral length.

4. The device of claim 1, wherein the implant is compressible and configured to expand in a direction of the longitudinal axis from a compressed state to a deployed state.

5. The device of claim 4, wherein the implant is configured to be retained in the compressed state by one or more compressing members.

6. The device of claim 1, wherein the first portion has a distal end that is distal from the second portion, and wherein the distal end is configured to be sutured on or close to a pelvic floor associated with the urethra.

7. The device of claim 1, wherein the implant comprises one or more loops that facilitate attaching the implant to one or more of the bladder, the urethra, and a pelvic floor.

8. The device of claim 1, wherein the implant comprises a memory shape material.

9. The device of claim 4, wherein the first portion and the second portion are removably coupled to one another.

10. The device of claim 1, wherein the implant has a substantially cylindrical shape.

11. The device of claim 1, wherein the implant comprises a tapered shape about the longitudinal axis that tapers outward from a first end of the implant to a second end of the implant, the second end being wider than the first end.

12. The device of claim 1, wherein the implant further comprises an antibacterial biomaterial.

13. A device for mitigating urinary incontinence post prostatectomy, the device comprising:
   a compressible implant configured to expand and compress along a longitudinal axis between a compressed state and an expanded state, the compressible implant having a first portion and a second portion that extend along, and are centered about, the longitudinal axis, the compressible implant forming a hollow interior area within the compressible implant that is centered about the longitudinal axis, wherein:
      the first portion and the second portion are each configured to form a tubular shaped wall centered about the longitudinal axis,
      the first portion is configured to receive a portion of a urethra therein, and
      the second portion is configured to receive an extended portion of a bladder therein; and
   wherein the compressible implant is configured to increase effective urethral length by extending and narrowing the extended portion of the bladder along the longitudinal axis while constraining the extended portion of the bladder within the hollow interior area of the compressible implant to mitigate stress that the bladder places on one or more sphincter muscles controlling passage of liquid from the bladder to the urethra and thereby mitigate incontinence.

14. The device of claim 13, wherein the compressible implant comprises loops that facilitate securing the compressible implant to one or more of the bladder, the urethra, and a pelvic floor.

15. The device of claim 13, wherein when the compressible implant is in the expanded state, the second portion has a tapered shape about the longitudinal axis that tapers outward from a first end of the second portion to a second end of the second portion, the second end being wider than the first end.

16. The device of claim 13, wherein the compressible implant is configured to be retained in the compressed state along the longitudinal axis by one or more compressing members.

17. A device for mitigating urinary incontinence post prostatectomy, the device comprising:
an implant having a first portion and a second portion, wherein the first and second portions are configured to form a hollow interior area within the implant extending along a longitudinal axis thereof, wherein:
the first portion and the second portion are each configured to form a tubular shaped wall centered about the longitudinal axis,
the first portion is configured to receive a portion of a urethra therein, and
the second portion is configured to receive an extended portion of a bladder therein, the second portion extending between a proximal end of the second portion and a distal end of the second portion wherein the proximal end is proximal to the first portion and has a width that is the same as a width of the first portion, and the distal end is distal from the first portion and has a width that is wider than the first portion; and
wherein the implant is configured to lengthen the extended portion of the bladder along the longitudinal axis by extending and narrowing the extended portion of the bladder while constraining the extended portion of the bladder within the hollow interior area of the implant to mitigate stress that the bladder places on one or more sphincter muscles controlling passage of liquid from the bladder to the urethra to thereby mitigate incontinence.

18. The device of claim 17, wherein the implant comprises loops that facilitate securing the implant to one or more of the bladder, the urethra, and a pelvic floor.

19. The device of claim 17, wherein the implant is configured to expand and compress along the longitudinal axis between a compressed state and an expanded state.

20. The device of claim 19, wherein the implant is configured to be retained in the compressed state by one or more compressing members.

* * * * *